United States Patent [19]

Baum

[11] 4,313,086
[45] Jan. 26, 1982

[54] METHOD AND APPARATUS FOR SEPARATING OIL AND WATER AND MEASURING THE AMOUNT OF OIL

[76] Inventor: Robert A. Baum, 1932 Altura Dr., Corona Del Mar, Calif. 92625

[21] Appl. No.: 20,719

[22] Filed: Mar. 15, 1979

[51] Int. Cl.$^3$ ............................................ G01N 27/42
[52] U.S. Cl. .................................. 324/65 R; 324/439
[58] Field of Search .................... 324/65 R, 439, 446, 324/448; 210/DIG. 26

[56] References Cited

U.S. PATENT DOCUMENTS 4,123,701 10/1978 Josefsen et al. ...................... 324/448

*Primary Examiner*—Ernest F. Karlsen
*Attorney, Agent, or Firm*—Fischer, Tachner & Strauss

[57] ABSTRACT

A method of measuring relatively small amounts of hydrocarbon oil contained in water, or other immiscible liquids including mixing a solvent and a conductivity additive with the oil and water or immiscible liquid, hereinafter termed "water" as it will be the most prevalent use, to form a mixture. The solvent is water rejecting and extracts the oil from the water. A method of producing a chemo-conductivity additive to render the electrically non-conductive oil of the mixture electrically conductive without rendering the solvent conductive or adding to any existing water conductivity. The amount of oil is electronically ascertained by measuring the conductivity of an electrical current passed through the mixture after the oil has been rendered conductive.

A novel apparatus is provided to perform the process. The apparatus comprises all the elements for carrying out the process including a separating funnel, measuring beaker, electrode assembly, electronics assembly and both analog and digital displays. In particular, the unique electrode assembly is specially designed to enable conductivity measurement of the electrically conductive-rendered oil.

5 Claims, 7 Drawing Figures

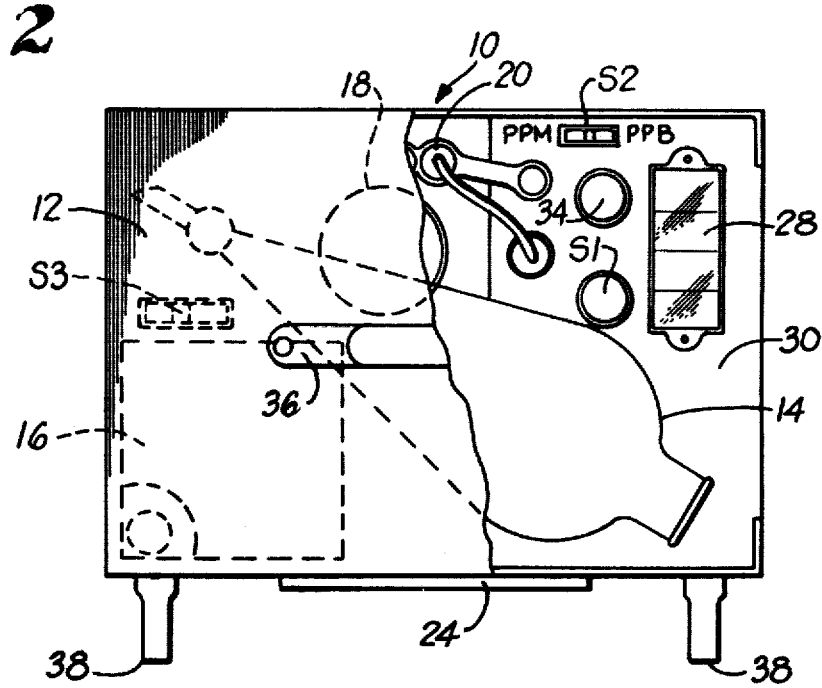
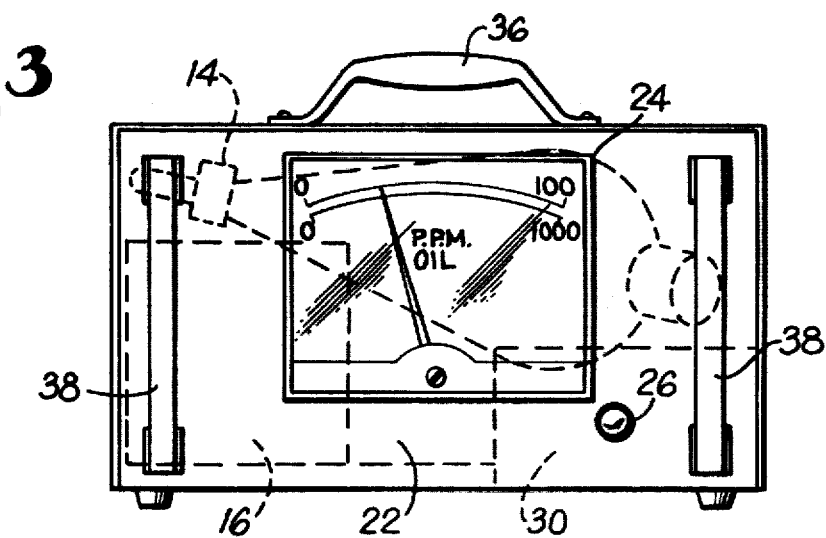

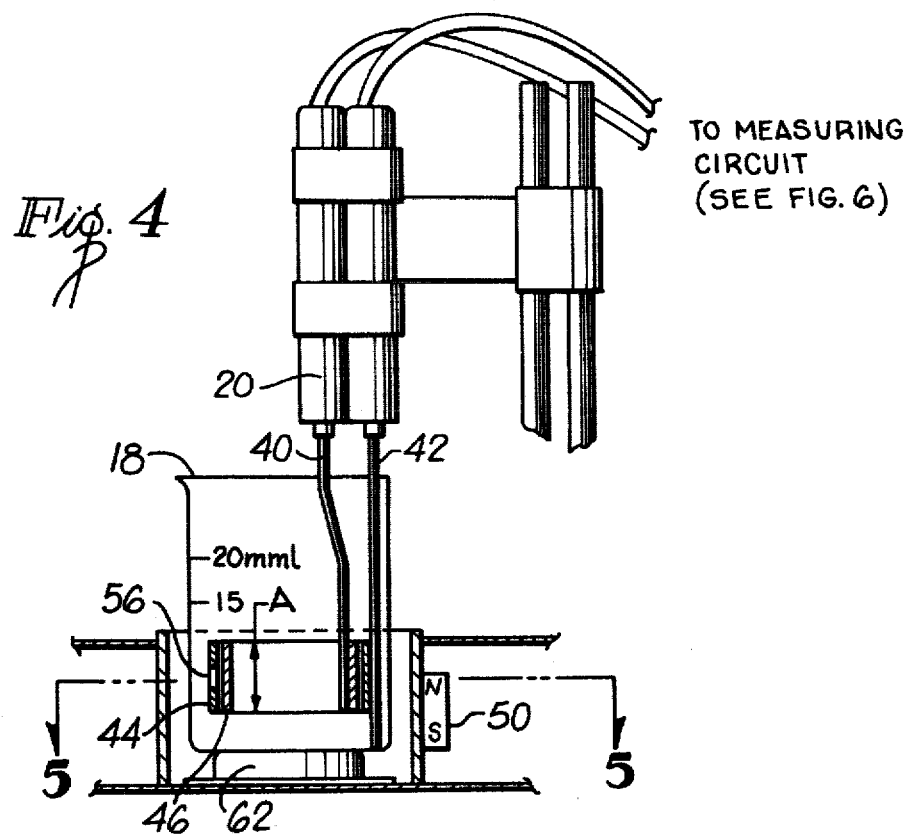
TO MEASURING
CIRCUIT
(SEE FIG. 6)
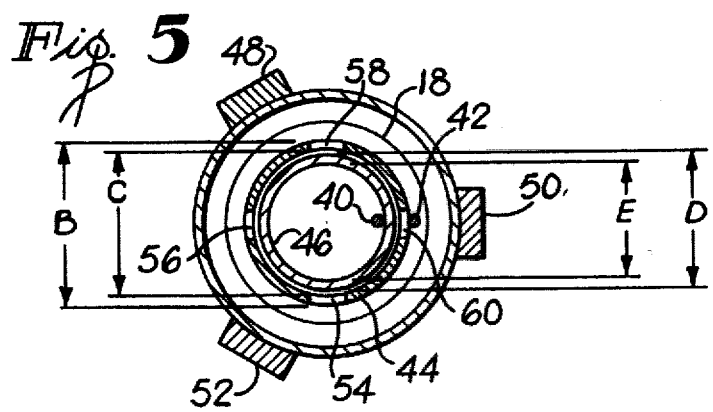

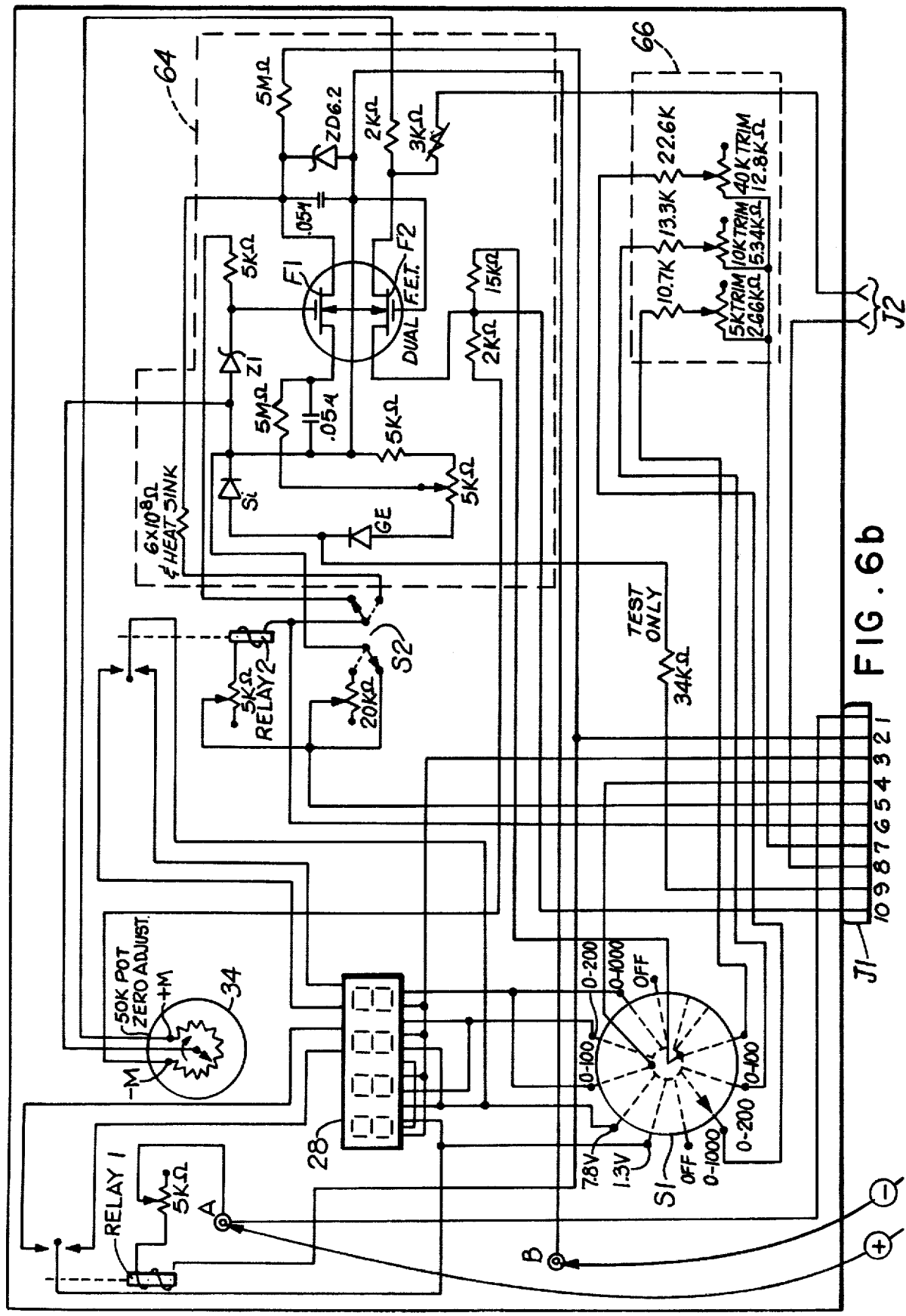

METHOD AND APPARATUS FOR SEPARATING OIL AND WATER AND MEASURING THE AMOUNT OF OIL

BACKGROUND OF THE INVENTION

Both unsaturated and saturated hydrocarbon oil in the parts per million or parts per billion range, is often present in water or in other liquids which are immiscible with oil. In many cases, various contaminants, such as salt, algae, silt, phenols, emulsifying agents, radioactive materials and other contaminants may be present. It is often necessary or desirable to measure the quantity of oil present in such a mixture. For example, it may be necessary to determine the amount of oil present in water being discharged to make certain that there is insufficient oil to have any deleterious effect on the environment. Also, it is sometimes desirable to monitor a liquid stream to determine if the quantity of oil present in the stream is sufficient to economically justify recovery of the oil. In addition, radioactive oil measurement can be of significant value.

The oil with which the present invention is primarily concerned is described herein as all saturated hydrocarbon oils, and those unsaturated oils which will not react in water by intermingling of atoms. For example, the oil may be crude oil or single or multiple saturated fractions thereof ranging, for example, from asphalt to clean lower-specific gravity crude to the very difficult to measure or treat "acid sludge" and/or BS&W present in the bottom of tanks as found in petroleum production. Also, the oil may be of the type obtained from petroleum refining and contain a wide series of hydrocarbons from distillation, including, for example, the paraffin series (methane series $C_nH_{2n+n}$), napthene or cycloparaffin series olefins ($C_nH_{2n}-2$ less H atoms), ethylene and aromatic series, and where the refinery has attendant chemical plants, oils from distillate based insecticides, etcetera.

Quantitative tests for oil in water or other liquids immiscible with oil are possible. For example, testing procedures using photometrics (in certain cases only) eight-hour hexane extraction in all cases, dyes (in certain cases only), infrared scan, spectrophotometry in all cases, conductivity (until this disclosure-useable in solvent-oil only), and others are known, but will not function in all cases, such as centrifuging, fluorescence, etcetera, as listed by the U.S. Department of Commerce S-85:950/SER:4324. However, these methods are carried out in a laboratory or in oxygen tests partially "fixed" in the field to hold sample enroute to laboratory, and this requires that samples be taken by skilled technicians, (if results are to be accurate, a service noted in all certified public testing laboratories' list of their function and costs), from a field location, which is often remote, to the laboratory, for testing. The time required for transporting the test sample and the test itself may result in substantial delay of the order of days between the time the sample is taken and the time the test results are obtained. Although some of the quantitative-oil-only testing equipment is purportedly portable, this equipment requires electrical power lines and so is not portable in the sense that it can be easily manually transported from location to location without requiring any external hook-ups of any kind, or the equipment may require a support system of such high weight or bulk as to be impractical to transport.

There are several portable oil monitors which use conductivity to measure the static charges on flammable liquids of a single composition. Information on these in the United States, United Kingdom, Germany, France and other countries has been studied and the manufacturers have reported that their devices will not operate where the sample to be tested for oil includes a mixture of water and oil and may contain more than one specific hydrocarbon fluid, particularly when the sample contains suspended debris.

SUMMARY OF THE INVENTION

This invention provides a new method and apparatus for determining the amount of saturated hydrocarbon oil and all unsaturated hydrocarbon oils that will not support a reaction in the presence of water or in a liquid immiscible with the oil. The apparatus is entirely portable and can be easily manually transported from location to location. As one of its novel features it is a light weight, and small support system having an electronic circuit which weighs 17 grams. The support system, case, supply of solvent, and power cells, in combination weigh less than 17 pounds (7711 grams). It may also be permanently installed if desired. When used as a portable unit, no external hook-ups, such as power connections, are required. Although the method of this invention can be carried out in a laboratory if desired, it is particularly adapted for the field at or near the location where the sample is taken. Although the described embodiment of the invention is sophisticated, it is also a rugged and simple instrument because of the use of micro-monolithic integrated substrates which obviate the use of all conversion charts, correction factors and mathematics permitting the tester to quantitatively obtain oil, and also perform the conversion functions. Thus the apparatus can provide a direct read-out and no special skill is required to operate the apparatus, to perform the method or to interpret the results.

Briefly stated, one aspect of the invention involves the separation of small amounts of hydrocarbon oil from an immiscible liquid, such as water. To obtain separation, a sample of the hydrocarbon oil entrained in the immiscible liquid is mixed with a solvent which is not soluble in the immiscible liquid and which extracts the oil from the immiscible liquid. The solvent not only extracts the oil, but rejects the immiscible liquid to form a solvent-oil mixture. The solvent-oil mixture has a higher specific gravity than the immiscible liquid so that the immiscible liquid and its dissolved and suspended solids float on the solvent-oil mixture within a mixing container. Materials that are inert or that will not remain in the immiscible liquid phase, form in a layer at the interface of the differing specific gravity liquids. The solvent-oil mixture can then be poured, drained, or otherwise removed, or partially removed, from the container. By removing less than all of the solvent-oil mixture, any contaminants present in the sample are left in the container.

Separation of the oil from the immiscible liquid and contaminants may be an end in itself, in that the aforementioned process provides clean oil in minutes by the "liquid filter" concept portion of this invention necessitated by a portable rapid result instrument whereas conventional filtration wherein a liquid is passed through a minutely porous solid media, a material such as agglutinous algae, would plug the porous "solid" media immediately. Another feature of the invention is to ascertain the quantity of oil present in the sample. To accomplish this, a conductivity imparting additive is mixed with the oil and the solvent. The conductivity additive is added in an amount that imparts a desired degree of polarity to bring the electronic circuit up to sufficient current passage to be stable and render the oil conductive. However, the solvent which is preferably essentially non-conductive, is not rendered conductive by the conductivity additive and the immiscible liquid is not rendered additionally conductive by the conductivity additive. It may appear that additional conductivity imparting to, for example, a water phase is not important as this phase is discarded after its oil has been extracted. However, this would remove some polarity imparting additive which would vary with each differing water phase or sample and thus a constant amount of polarity imparter would not be available for the oil phase and cause innaccurate results. Water distilled 18 times in quartz glass has a dielectric constant of 80.37 at 20 degrees centigrade whereas petroleum oil has a dielectric constant ±2.0 at 20 degrees centigrade or 0.025 as much. An electric current is then passed through the conductive oil mixture to obtain an indication of the amount of oil in the mixture.

It has been found advantageous to utilize a pair of concentric ring-shaped electrodes to pass the electric current through the conductive oil mixture as largest area in smallest space is obtained. These electrodes are of equal area obtained by placing equidistant circular holes of a total area equal to the difference between the areas of the outer circle and the inner circle thus making each electrode of equal size as well as providing better liquid flow through the electrode gap. The electrodes can be spaced very closely, for example, at a one millimeter gap, thus perfect concentricity is not required as at ever closer proximity it has been ascertained that the average spacing between the electrodes becomes determining by the law of diminishing returns. This averaging effect is not limited to concentric circular electrodes but applies to flat plates and other configurations as well.

Such a feature is of particular value in a portable, typically roughly handled apparatus, and is particularly advantageous in a system designed to indicate parts per million or parts per billion oil. The conventional one centimeter spacing used to provide volumetric units in cubic centimeters, would be disadvantageous because a lack of concentricity of the spaced plates of the electrodes would be determining. In this instance however, the smaller gap might at first glance present a problem because of the use of a conductive additive of finite but colloidally dispersed metal or metal compound which is attached to the petroleum oil and produces a fluid with poor circulation due to greater friction between close surfaces, as well as a tendency of the charges to orient themselves North and South with respect to the current flow. The result would be meter drift towards less conductivity. However, the instrument is designed to include three Alnico IV permanent magnets oriented equidistantly outside the glass vessel (25 ml beaker) container and their resultant magnetic field pushes the electrons to yield a fluid mixture having sufficient circulation to prevent such meter value drift.

This is a novel concept in electrodes. However, it is a proven concept in research in other arts. By way of example, a cyclotron operates on a similar principle in which continued magnetic force "kicks" causes neutrons to move ever faster until almost reaching the speed of light.

Prior art, disclosed in earlier patents (by way of example, see U.S. Pat. No. 2,518,758), relates to inventions currently used in laboratory work, involves a far less efficient method, inappropriate for field use, and consists of the use of a slave magnet inert bar placed on the bottom of the vessel. Outside the vessel bottom a motor driver rotating another magnet, drives the slave magnet in the liquid thus providing mechanical stirring.

The above disclosed, entirely self-supporting magnetic motion imparter, is a unique concept developed for the particular needs of a portable oil tester. However, the above disclosed unique magnetic motion imparting concept is not to be limited to use in the presently disclosed invention, but may, as those familiar with the art will now understand, be used in other systems not necessarily relating to the present invention.

By extracting the oil from 200 milliliters of sample into 20 milliliters of solvent, a concentration oil factor of X10 was obtained. However, now it will be understood that the unique electrode of the present invention also provides a gain in oil concentration of additional factor by spacing the electrode plates one millimeter apart as opposed to the standard 1 centimeter. Experimentation by the applicant has shown that the decrease in plate spacing produces a non-linear result and an actual gain factor of 22.5 times in concentration of oil presented to the electronic measuring circuit of the present invention.

The instrument includes an electrical circuit which enables a direct read-out of the quantity of oil present in the sample on various scales, including parts per million and parts per billion.

The invention, together with further features and advantages thereof, may best be understood by reference to the following description taken in conjunction with the accompanying illustrative drawings.

BRIEF DESCRIPTION OF THE DRAWINGS

FIGS. 2 and 3 are more detailed top and front views, respectively, of the apparatus illustrated in FIG. 1;

FIGS. 4 and 5 are plan and elevation views, respectively, of a portion of the apparatus of the present invention illustrating the manner in which certain steps of the inventive process are carried out; and FIG. 6, comprising FIGS. 6a and 6b, is a detailed schematic diagram of the electronics portion of the present invention.

DETAILED DESCRIPTION OF THE INVENTION

Figure 1:
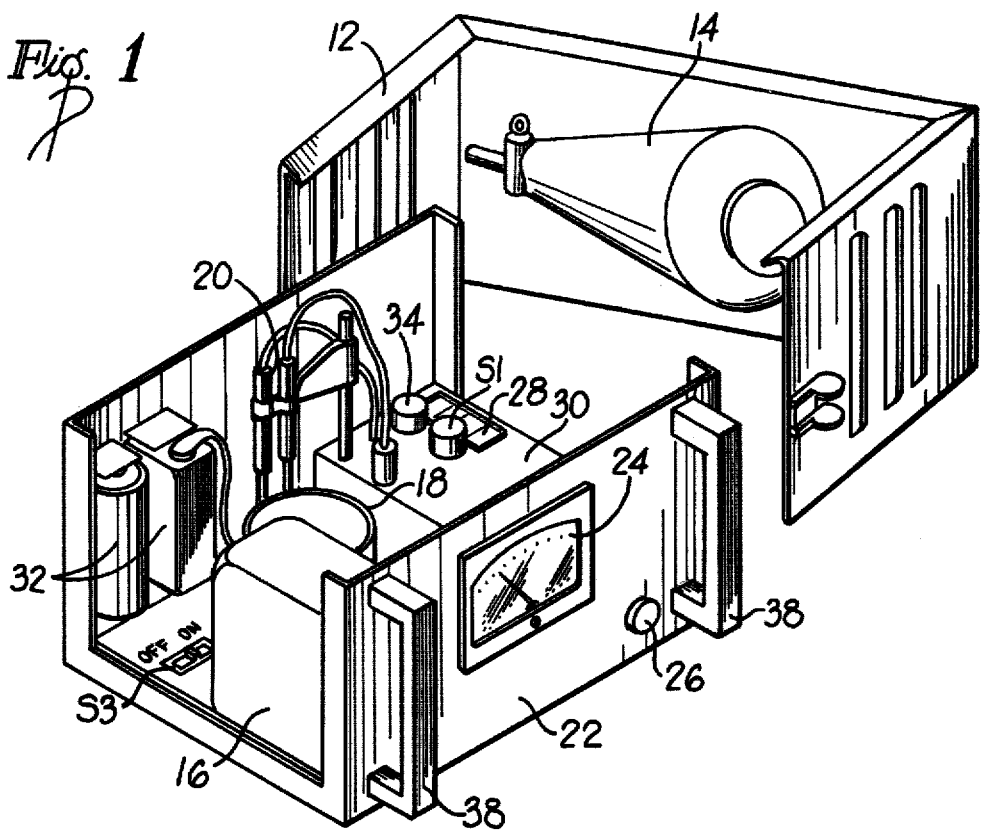
FIG. 1 is a three dimensional view of an embodiment of an apparatus used for carrying out the process of the present invention.

The first step in the process of this invention is the extraction of oil from water or other immiscible liquid and suspended solids. Hydrocarbon oil tends to float on water, and so extraction of the oil where large amounts of it are present, such as a contiguous layer, can be done in many obvious ways. However, when oil is present in parts per million range, such as one to one thousand parts per million or in the parts per billion range, such as occurs in radioactive oils, the presence of the oil may not be discernable or quantitatively judged by the naked eye. In this situation, the extraction of the oil from the water is a much more difficult problem.

The oil can be advantageously extracted utilizing a solvent which is essentially not soluble in the immiscible liquid, and the extraction of oil from water using tetrachloromethane, (CCl₄) hexane, petroleum ether, etcetera. The solvent extracts the hydrocarbon oil and rejects the immiscible liquid, and also rejects solid or dissolved solids in water and the contaminants or debris. By mixing the solvent with a sample containing saturated hydrocarbon oil (or unsaturated hydrocarbons that will not enter into any type of relation with water) and the immiscible liquid, the solvent extracts the oil from the liquid to form a solvent-oil mixture. The degree to which the solvent rejects water can be varied to a very small degree, however, the solvent preferably has a water rejection constant in the range of $0.08^{20}$, water content.

To bring about separation of the solvent-oil mixture from the immiscible liquid, the mixture and the liquid preferably have different specific gravities. Thus, following mixing, the heavier component settles to the bottom of the mixing container, and the lighter component physically separated from the solvent-oil mixture drained from the container. For field testing a 75% withdrawal is preferred as this leaves 25% in the cone shaped vessel so that the operator does not have to make an exact removal. This separation of the oil from the immiscible liquid may be an end in itself or additional operations may be performed on either or both of the separated components.

In addition to the characteristics noted above, the solvent is also preferably inflammable or at least of low-vapor pressure. When the extraction of oil is for the purposes of measuring the amount of oil in the sample, then the solvent should be essentially non-conductive. For example, the solvent may have an electrical conductivity of the order of $4 \times 10^{18}$ or a dialectric constant of approximately 2.2 or less. Various solvents usually of the chloro hydrocarbons, including the solvents set forth in the table below meet these requirements:

| Solvent | Sp. Gr. at 20° C. | H₂O Reject Constant | Conductivity as Dielectric Constants | Flam. | Viscosity |
|---|---|---|---|---|---|
| tetrachloromethane/ CCl₄ | 1.595 | $0.08^{20}$ | 2.238 | 0 | 0.96 |
| tetrachloroethylene/ C₂Cl₄ | 1.631 | 0.00 | 3.400 | 0 | 0.90 |
| tetrachloroethane/CHCl₂—CHCl₂ | 1.602 | 0.003 | 7.800 | 0 | 1.60 | nents rises. Thus, the resulting solution is layered, with the solvent-oil mixture being in one layer and the immiscible liquid being in a second layer.

Preferably, the solvent-oil mixture has a higher specific gravity than the specific gravity of the immiscible liquid to assure that the immiscible liquid will float on the solvent-oil mixture. One important advantage of this is that many of the contaminants, such as silt, algae, etc., tend to float on the top of the relatively high specific gravity solvent-oil mixture. More specifically, the contaminants characteristically float at the interface between the solvent-oil mixture and the immiscible liquid. Thus, not only is oil separated from the immiscible liquid, but also from the contaminants contained in the sample.

Because the solvent-oil mixture is primarily made up of solvent, the specific gravity of the mixture is essentially the same as the specific gravity of the solvent. In order that the immiscible liquid and the contaminants will float on the solvent-oil mixture, the specific gravity of the solvent must be selected in relation to the specific gravity of the immiscible liquid. For example, when the immiscible liquid is water, the specific gravity of the solvent is preferably in the range of 1.3 to 2.5 or greater with a specific gravity of approximately 1.6 being preferred.

The amount of solvent used for test is calculated on the highest testor concentration of oil range of the test instrument. Much higher ranges can be set, but usually that is unnecessary. The volume of solvent mixed with the sample is also preferably sufficient to provide a layer of the solvent-oil mixture of workable thickness in the container. This facilitates physical separation of the solvent-oil mixture from the immiscible liquid by draining the former from the bottom of the container. By draining less than the full amount of the solvent-oil mixture from the container the P.P.M.'s are not changed, the contaminants are left in the container Although the solvent and the immiscible liquid can be mixed in different ways, preferably they are mixed in a transparent mixing container having a drain valve at the bottom and a fill opening at the top which can be suitably closed as by a stopper. The mixing container preferably has graduations so that a representative sample of any one of a number of known volumes can be poured into or otherwise provided in, the mixing container. The solvent is poured from a container, such as a beaker, through the fill opening into the mixing container. The fill opening is closed with the stopper, and the solvent and sample are manually and violently shaken up and down for a time, such as 30 seconds, which is normally sufficient to completely mix the solvent and the sample. At least once during this mixing period, the agitation is terminated and the stopper momentarily removed to vent any gas pressure within the mixing container.

After termination of the agitation, the mixing container is manually moved in a circular manner to give the sample and solvent a swirling motion until the heavier solvent-oil mixture settles to the bottom of the mixing container and the lighter immiscible liquid floats on top of the mixture. When the immiscible liquid is water, it is ordinarily clear, although depending upon the particular sample, it may be somewhat cloudy. The solvent-oil mixture, on the other hand, has a brownish color. If the upper phase of the mixing container does not become clear of brown color, the agitation should be continued until the upper layer becomes relatively clear. If the upper layer does not become clear with continued agitation, then insufficient solvent has been added to extract all of the oil from the sample. For example, if the amount of solvent added was sufficient to extract 1000 ppm of oil and the upper phase remains brownish after continued agitation, the sample contains over 1000 ppm of oil. This can be used, if desired, as a quick go-no go test for the amount of oil contained in the sample.

The solvent-oil mixture can be utilized in accordance with the teachings of this invention to determine quantitatively the amount of oil in the sample. To accomplish this, a conductivity additive is mixed with the oil and the solvent. Preferably, the conductivity additive and the solvent are pre-mixed and are mixed together with the sample using the procedure described above to substantially simultaneously achieve extraction of the oil from the sample and the rendering of the oil conductive. However, if desired, the conductivity additive may be added after addition of the solvent.

An important characteristic of the conductivity additive is that it must make the oil conductive while leaving the other components, e.g., the immiscible liquid, the debris and the solvent, non-conductive.

When the conductivity additive, the oil and the solvent are mixed, the oil is rendered electrically conductive, and the solvent remains essentially non-conductive. As the oil is the is the only electrically conductive component of the resulting mixture, the amount of oil in the sample can be measured by passing an electric current through the mixture. Accordingly, the greater the quantity of oil, the more current that can be carried through the mixture for a given voltage.

It is important that the conductivity additive not render the solvent electrically conductive. If both the solvent and the oil were conductive, it would not be possible to accurately determine the amount of oil present from the conductivity of the resultant mixture because the oil would characteristically form only a small percentage of the total mixture.

The conductivity of the oil increases with increased volumes of conductivity additive up to a threshold. Beyond the threshold, addition of more conductivity additive will not increase the conductivity of the oil. However, it will not have any deleterious effect. Accordingly, the preferred amount of conductivity additive is the amount which raises the oil to its maximum conductivity level.

Various kinds of conductivity additives which meet these requirements can be used. For example, colloidal metal-containing particles can be used to render the oil conductive without rendering the solvent conductive. The colloidal metal particles can advantageously be dispersed in the solvent which is used to extract the oil and should be of a size small enough to remain permanently dispersed in the solvent. For example, particles having one dimension no greater than 0.2 microns will remain in suspension in the solvent for long periods. It is believed that the colloidal metal-containing particles are adsorbed on the hydrocarbon oil without penetrating the oil molecule. This imparts conductivity to the oil without rendering the solvent conductive.

Various conductive metal-containing particles which are not soluble in the solvent and the water phase can be utilized, such as chromium dicarbide ($Cr_3C_2$), chromium silicide ($Cr_3Si_2$) and silver peroxide ($Ag_2O_2$).

A colloid is a finite solid particle insoluble in its dispersal medium which will not combine or be absorbed with the dispersal medium and should not be capable of being filtered out. The stable hydrophobic colloidal particles of suitable metal compounds with their inherent excess atoms appear to be in true solution as a refractive plane or even Tyndal effect does not reveal them. When the solvent and its solvent-rejecting colloid additive are mixed with saturated hydrocarbon oils at the same time, it is believed that the excess negative charged colloid is adsorbed on the static oil and unbalances its charges. The unbalanced charges seek balance, and the non-polar charges are forced to move. When movement of charges occurs, the oil is no longer highly non-polar, but rather has a degree of polarity of conductance for charge movement sufficient to measure electronically.

Many metals can be rendered colloidal. However, to be used with oil and be adsorptive, solvents and metal-containing particles must be insoluble in water in the oil extraction solvent. Furthermore, the colloidal metal-containing particles should have a dielectric constant higher than petroleum oil at $2 \times 10^{16}$ r/$CM^3$ where r is resistivity in Ohms and have excess negative charges. Alkaline earth metal oxides that form hydrophilic hydro oxides which are water bonded, should not be used. It is preferred to disperse a single alkaline earth metal rather than a mixture of metals, and it should be combined as an insoluble irreversible compound from which a gel is made by mechanically reducing to less than 0.2 microns. This enables dispersion of the colloidal metal containing particles without chemical assistance.

An alternative to the use of colloidal metal containing particles is the conductivity additive described in U.S. Pat. No. 3,126,260. This patent discloses a conductivity additive in the form of an organic composition which consists essentially of a salt of a polyvalent metal and an alkylated salicyclic acid containing at least one alkyl substituent having eight or more carbon atoms and a polymeric material which is soluble in the organic liquid and which contains at least one acid group. The polyvalent material may be, for example, chromium, and the polymeric material is not essential. One such conductivity additive is available from Shell Chemical Company as ASA-3 Anti-Static Additive.

Figure 6A:
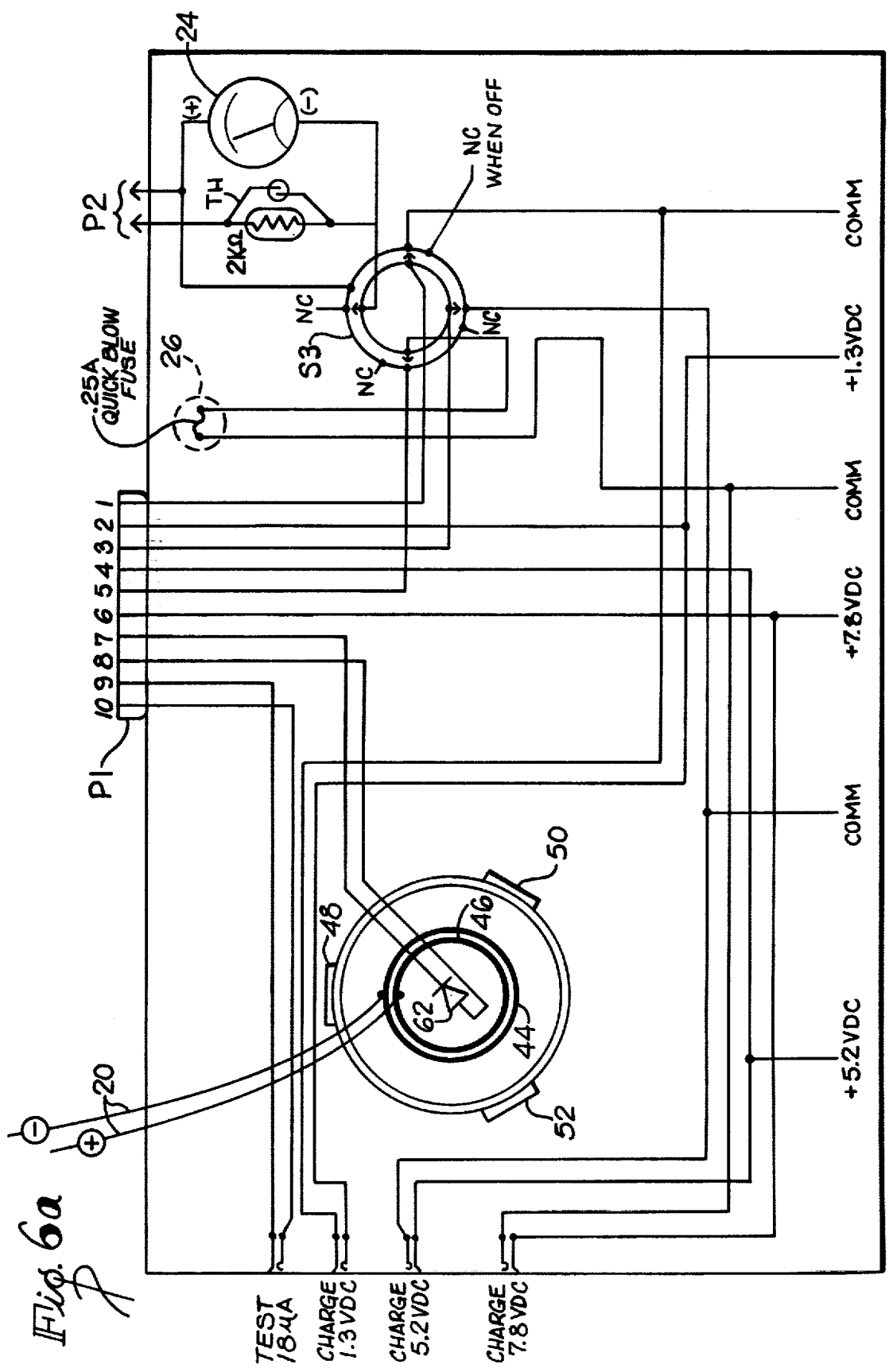

Having extracted the oil from the sample and rendered the oil conductive, the quantity of oil in the sample can be determined by passing an electric current through the mixture utilizing the apparatus shown in FIGS. 6a and 6b. One advantage of this invention is that it provides a method and apparatus for measuring accurately extremely small volumes of oil in the sample. It is important to note at this juncture that one factor contributing to this advantage is that the oil is, in effect, concentrated as a result of the extraction of the oil from the sample. For example, if the original sample contains 200 milliliters and 20 milliliters of solvent are added to the sample, then all of the oil originally contained in a 200 milliliter volume is now concentrated in a 20 milliliter volume of solvent. Thus, in this particular example, the oil extraction step concentrates the oil on a volume basis by a factor of ten, and this facilitates the taking of conductivity measurements.

Now that the steps comprising the inventive process of the present invention have been delineated in detail, a novel apparatus for performing that process will now be described in conjunction with FIGS. 1 through 6.

As indicated in FIG. 1, the portable oil monitoring apparatus 10 of the present invention is an entirely self-contained unit comprising all the apparatus to carry out the steps of the process described above.

As FIG. 1 illustrates, monitoring apparatus 10 includes a cover 12 which is fitted to enclose the top of the apparatus to protect the interior components at times when the apparatus is either being stored or carried to and from the field site. Further shown in FIG. 1 is a separating funnel 14 that is conveniently mounted by appropriate brackets against the inside top wall of cover 12. In addition, a solvent container 16 and a measuring beaker 18 are also included so that all the devices for taking a sample, mixing the sample and producing the appropriate ratio of solvent and sample are readily available to the user along with the apparatus for measuring the parts per million or parts per billion of oil in the sample as will be hereinafter described.

The remaining elements of the apparatus, as viewed in FIG. 1, come into play in the novel process of the present invention in actually measuring the conductance of the prepared test sample. These elements include an electrode assembly 20, an instrument front panel 22 upon which are mounted a current meter 24 and a fuse holder 26, digital display 28, electronic circuits mounted on a printed circuit board within assembly 30, appropriate power cells 32 to power the unit in the field away from any form of electrical power source and potentiometer 34 which is used to provide appropriate adjustments to the circuit to achieve an accurate reading of the oil content on current meter 24 and digital display 28. Meter face roll bars 38 protect the meter from adjacent objects against which apparatus 10 may be stored.

FIGS. 2 and 3 provide more detailed views of the fully assembled instrument of the present invention with cover 12 in place and the unit in condition for being carried to the site for the oil measurement. In FIG. 2 cover 12 is shown partially broken away to reveal separating funnel 14 in its stored position, electrode assembly 20, electronics assembly 30, digital display 28 and potentiometer control 34. In addition, one may observe partially exposed measuring beaker 18. On the left side of FIG. 2 and shown in dotted lines, is solvent container 16. In addition FIG. 2 provides a top edge view of the current meter 24. These same components of the portable oil monitor 10 are illustrated in front view in FIG. 3 which provides full frontal view of current meter 24 and the meter face roll bars 38 mounted to the left and right most portions of the front panel 22.

FIGS. 4 and 5 provide more detailed views of the electrode assembly 20 and the manner in which the electrode assembly is utilized to apply a known voltage across an electrode gap of predetermined dimensions to induce a current through the test solution. The magnitude of that induced current, when sensed by the measuring circuit to be described hereinafter in conjunction with FIG. 6, provides a direct indication of the relative amount of oil contained in the test sample.

As shown in FIG. 4 electrode assembly 20 includes a pair of electrode connector rods 40 and 42. The shorter of the connector rods, 40, is electrically affixed to the inner-most of two, concentric, circular cylinder electrode rings. The longer electrode connector rod, 42, is electrically affixed to the outer concentric electrode ring 44 and extends beyond the bottom of the electrode rings to provide a convenient spacer between the electrode rings and the bottom of measuring beaker 18. In the preferred embodiment of the invention, the electrode rings are about ½ inch in height, (dimension A in FIG. 4), outer ring 44 has an outer diameter of 27.587 millimeters (dimension B) and an inner diameter of 26 millimeters, (dimension C) while the inner ring 46 has an inner diameter of 22.413 millimeters (dimension D) and an outer diameter of 24 millimeters (dimension E). Thus the spacing between rings 44 and 46 is about 1 millimeter measured radially from the center of the concentric rings.

Three permanent magnets 48, 50 and 52 are spaced equidistantly around the outside of beaker 18 to reduce measurement drift problems. As shown in FIG. 4, the north pole of each magnet is oriented at the top of the magnet. A suitable selection for magnets 48, 50 and 52 is ALNICO No. 4. As also previously discussed, the outer ring 44 has four equidistantly spaced apertures of circular cross section. The combined area of these apertures is equal to the difference in surface area of the two rings. These four apertures 54, 56, 58 and 60, in addition to providing means for equalizing the ring areas, also provide for improved test sample flow within the gap between the rings.

At the lower most portion of FIG. 4 it may be observed that a temperature sensor diode 62 is located below and in contact with beaker 18. This germanium temperature sensor diode is connected to the measuring circuits, as will hereinafter be described in conjunction with FIGS. 6a and 6b, to provide a means for compensating for temperature variations in the test sample so that the current measured between outer ring 44 and inner ring 46 through the test sample is relatively insensitive to such temperature variations.

Reference will now be had to FIG. 6, which comprises FIGS. 6a and 6b, and which is a detailed schematic diagram of the electronics assembly 30 and interface components of the present invention. The purpose of the electronics portion of the invention is that of providing a means for reading the current induced in the gap between electrode rings 44 and 46 through the test solution, in terms of parts per million or parts per billion oil.

Upon analysis of FIG. 6 by those having skill in the electronics art, it will be clear that the principal purpose of the circuit therein illustrated is that of applying the current induced across the test sample between electrode rings 44 and 46 to a differential amplifier circuit 64 and the amplified output thereof to a monitoring device, in this case both meter 24 and digital display 28. Additional portions of the electronics 30 of the present invention include the switches S1, S2 and S3 for turning the system on by applying DC power available from stored power cells to the electronics and for selecting the appropriate meter range, namely, 0 to 100 parts per million, 0 to 200 parts per million, 0 to 1000 parts per million and 0 to 100 parts per billion. Switch S1 is accessible at the top of electronics assembly 30 adjacent digital display 28 and zero adjust 34, (see FIG. 1 and 2). Switch S2 is accessible at about the same location but on the other side of zero adjust 34, (see FIG. 2). Switch S3 is accessible adjacent solvent container 16, (see FIGS. 1 and 2).

A trimmer resistance circuit 66 includes the appropriate fixed and variable value resistances to calibrate the readings for these various ranges. Other adjustable potentiometers are included to zero the meter and display readings and to adjust the operating parameters of amplifier circuit 64 for proper circuit operation. In addition two relays are provided, namely, relay 1 and relay 2 which are automatically activated when the power cell voltage levels fall below the values needed to provide accurate measurement readings of the test sample conductivity. In addition four externally available circuit terminals are provided to permit recharging of the rechargeable power cells when their respective power levels diminish below acceptable voltage levels and also to provide a means for applying a test current to the meter through amplifier circuit 64 for maintenance and calibration purposes.

As shown at the lower portion of FIG. 6a, three different voltage levels, namely, 5.2 volts DC, 7.8 volts DC and 1.3 volts DC are used to power the electronics. These voltage levels have been selected so that one may readily use commercially available 1½ volt and 9 volt rechargeable power cells, which as commonly known, actually provide reliable voltage levels of 1.3 volts and 7.8 volts, respectively. The 5.2 volts DC power source, which may be provided by combining four 1½ volt rechargeable batteries in series, is used to provide the power necessary to drive digital display 28. On the other hand, the 7.8 volts DC which may be provided by utilizing a 9 volt rechargeable cell, or if desired, a plurality of such cells in parallel to extend the operating time of the instrument between recharging cycles, and the 1.3 volt DC power source which may be provided by a 1½ volt rechargeable power cell or a plurality thereof in parallel for the same reason, are utilized in the apparatus to provide a known voltage level of 9.1 volts DC and to also provide the voltage levels to power differential amplifier circuit 64.

Meter 24, shown in the upper right hand corner of FIG. 6a, may be protected from high voltage transients and the like by means of a thyristor TH and is connected to the remaining portion of electronics assembly 30 by means of a four-pole, double-throw switch S3. One suitable meter for use in the present invention is an 18 micro amp d'arsonval, two jewel, four inch needle movement meter. Switch S3, when in its on configuration, applies the power cell voltages to the circuit to permit use of the electronics for test purposes, and when in an off condition, removes the power and shorts the meter for protection thereof. In the off condition of switch S3, the power cells, if they are of the rechargeable type previously discussed, may be recharged by applying suitable voltages from external sources to the aforementioned terminals shown in the left portion of FIG. 6a.

FIG. 6a also shows the manner in which the electrode assembly 20 is connected into the electronic assembly 30 of FIGS. 6a and 6b. The circuit elements shown in FIG. 6a including meter 24, switch S3, the electrode assembly and power cell lines, are all appropriately connected to a 10 pin plug P1 and a two terminal plug P2, both of which have corresponding mating jacks J1 and J2, respectively, shown in the lower-most portion of FIG. 6b. A 0.25 amp quick-blow fuse is also included in the circuit of FIG. 6a to provide circuit protection. As previously indicated, this fuse is accessible at the front panel by means of fuse holder 26 as discussed previously in conjunction with FIGS. 1 and 3.

Reference will now be made to FIG. 6b for a more detailed indication of the manner in which the current through the electrode gap provides a measurement readout. The objective of the circuit of FIG. 6b is to provide a measurement of the current induced across the electrode gap in response to the application of a known fixed voltage to the circuit in which the gap forms a part thereof. As previously indicated, this current has been made relatively insensitive to temperature by means of a germanium diode 62 sealed in a TO3 can and located at the bottom of beaker 18. It has been found that the temperature can vary from at least as low as minus 40 degrees Fahrenheit ($-40°$ F.) to as high as plus 176 degrees Fahrenheit ($+176°$ F.) without substantially affecting the accuracy of the measurement, because of the voltage drop compensation versus temperature characteristics of the germanium diode.

As shown at the left-most portion of FIG. 6b, the electrode rods are connected to terminals A and B of the circuit. Terminal A is connected through junction plug J1 to ground and the voltage at terminal B varies in accordance with the current level through the electrode gap. Thus, the voltage variations at B reflect the variation in conductance of the test sample in accordance with the oil content thereof. The voltage level at terminal B is applied to the gate electrode of FET F2 of the dual FET device within differential amplifier circuit 64. Furthermore, when switch S2 is in the parts per million position, which is the position illustrated in FIG. 6b, the gate terminal of FET transistor F1 is tied to a voltage level of 6.2 volts by means of 6.2 volt zener diode Z1 which is in series with a 5 Kohm load resistor in the gate circuit of FET F1.

It is the difference in the voltage levels applied to the respective gates of FET transistors F1 and F2 that is determinative of the voltage ultimately applied, after suitable attenuation for zero adjustment in potentiometer 34, to the meter and to the digital display 28 for a reading that is directly indicative of the oil content of the test sample. The difference voltage applied to the respective gates is amplified by the FET circuit and the amplified signal is applied to the respective source terminals of the FET transistors F1 and F2 which are in turn applied between a fixed terminal and the variable position terminal of 50 Kohm potentiometer 34, the position of which determines the total voltage drop across the two fixed terminals of potentiometer 34.

The +M terminal of potentiometer 34 is connected through a voltage divider network to the positive terminal of meter 24 through jack J2, while the −M terminal of potentiometer 34 is connected through switch S1 to the appropriate trim resistor value in trim resistor network 66 to the negative side of the meter by means of jack J2. There are three such trim resistor values corresponding to the three switch values for the ranges 0 to 100, 0 to 200 and 0 to 1000 parts per million oil, respectively.

When switch S2 is thrown to the position indicated by dotted lines in FIG. 6b, the bias voltage at the gate terminal FET F1 is reduced considerably by removing the 7.8 volts DC from the series load resistor connected to zener diode Z1 thereby substantially increasing the voltage difference applied to the meter 24, and making the meter more sensitive to the subtle changes corresponding to conductivity variations for oil levels in parts per billion. In the parts per billion mode, in the embodiment of the invention illustrated in FIG. 6b, switch S1 is positioned to be in the zero to 100 range.

The 1.3 volt power cell output is applied to one side of the coil of relay 1, the other side of the coil being connected to ground potential through a variable resistor. Similar connections made to the 7.8 volt power cell output at relay 2. The two variable resistors associated with the relays are adjusted so that when one or both of the power cell levels drops below a predetermined voltage, the relays are deactivated and digital display 28 reflects the low voltage situation.

The remaining elements in FIG. 6b are primarily for biasing the differential amplifier circuits at the appropriate levels to provide accurate readings corresponding to the oil content measured in the test sample and to connect display 28 to the appropriate terminals to read and display digital representations of the oil content and also of the power cell voltage levels during maintenance and calibration of the instrument.

Now that the chemical and electrical aspects of the process and apparatus of the present invention have been described in detail, typical operation of the invention will be disclosed.

It will be recalled that the apparatus of the present invention has been developed for field use such as maintenance or daily inspection. For example, it would be readily useable by petroleum production field service personnel wherein one individual employee is responsible for a block of, for example, 100 oil wells, pumps, piping, tanks, oil and water drains and reports to a supervisor when his shift ends. It is contemplated that under certain circumstances there will be a definite program of periodic testing requested by such supervisor to ascertain if the tank or any portion of the well block is losing petroleum oil in significant quantities to be of economic value if recovered and/or in an amount that exceeds environmental regulations.

When the employee reaches the test site, the test unit is placed on reasonably level ground and the 16 gauge steel cover 12 removed from the apparatus. The 250 milliliter pyrex glass separating funnel 14 is then removed from the clamps holding it inside the cover 12. At this point the first test sample is taken by holding the separating funnel under the appropriate discharging pipe or by dipping it into a drainage trench as required to recover the sample. This is preferable to obtaining the sample with one container and pouring it into a separate sample bottle, since a large error in oil content may occur with use of two vessels in which some oil will adhere to the sides of the first container when the sample is poured into the second.

Sufficient sample fluid is taken into the separating funnel 14 to fill the funnel to the 200 milliliter mark. The solvent and polarity imparter from solvent container 16 are added to the extent of 20 milliliters to the sample in the separating funnel and the entire contents, with stopper in place, are shaken up and down for about 30 seconds to provide maximum interface between the sample liquid and solvent. Then the separating funnel contents are swirled to aid in consolidating the oil. At least once during violent agitation, the glass stopper of the separating funnel is removed to vent any gases. If the water phase floating on top of the solvent-oil sample shows a faint brown color of oil, the operation should be repeated.

When the separating funnel shows 20 milliliters or more of oil and solvent at the bottom thereof, the funnel valve is opened and beaker 18 is filled to the 15 milliliter line. This leaves 5 milliliters of solvent in the narrow taper end of the separater funnel 14 that can be seen clearly. By leaving this additional 5 milliliters of solvent in the funnel, the operator does not have to use extraordinary skill to stop the valve at the exact liquid-liquid zone. The sample is now ready to test.

The portable oil monitoring apparatus is turned on by setting switch S3 (See FIG. 1) to the ON position. Then range selector switch S1 (See FIG. 1) is switched to the appropriate range of oil parts per million and potentiometer 34 is set to zero the meter at this range. The meter will quickly reach its reading, allowing the operator to note the oil content and record the results. If both the meter and display read zero with electrode assembly 20 immersed in the test solution in beaker 18, an attempt should be made to read oil content in parts per billion by selecting that mode by means of switch S2 as discussed above in conjunction with FIG. 2.

Examples of actual tests conducted with the inventive apparatus and in accordance with the steps of the novel process, will now be described.

EXAMPLE I

A 200-milliliter sample of water, suspended solids, and 90 parts per million (ppm) oil was placed in a mixing container. 20 milliliters of tetrachloromethane solvent already mixed with the polarity imparter was added to the sample and manually, violently agitated up and down in the mixing container for a period of 30 seconds. After 15 seconds of agitation, the stopper in the mixing container was removed instantaneously to vent gas pressure within the mixing container. Following the 30 seconds of agitation, the mixing container was moved in a circular motion to swirl the mixture for another 30 seconds. At the end of the second 30-second period, the mixture in the mixing container was separated into a brownish lower phase and a clear upper phase. Suspended solids were visible to the naked eve at the interface of the two phases. 15 milliliters of the lower phase was drained out through a drain valve at the bottom of the mixing container leaving the upper phase and the suspended solids in the mixing container.

EXAMPLES II and III

The procedure described in Example I above was repeated first with tetrachloroethylene used in lieu of tetrachloromethane and secondly with tetrachloroethane used in lieu of tetrachloromethane. The results obtained were the same as described above in Example I.

EXAMPLE IV

To determine the amount of oil in a 200-milliliter sample of oil, suspended solids and water, chromium dicarbide particles of 0.2 microns size were provided by mechanically reducing the material to 0.2 microns or less. The colloidal particles were then mixed with tetrachloromethane to provide a colloidal gel. Three parts by volume of the colloidal gel was then mixed with 97 parts by volume of tetrachloromethane. 5.1 milliliters of this mixture were then mixed with 24.9 milliliters of the solvent to provide a solvent conductivity additive mixture.

The procedure described in Example I above was then repeated using the solvent conductivity additive mixture in lieu of the solvent of Example I, and 15 milliliters of the brownish lower phase was drained through the drain valve at the bottom of the mixing container back into the beaker used for introducing the solvent-conductive additive mixture to the mixing container. This left the suspended solids within the mixing container. An electric current was then passed through the 15 milliliters of brownish lower phase material using the apparatus described above in conjunction with FIGS. 1 through 6, readout on the dial of the apparatus showed 90 ppm of oil.

It will now be apparent that what has been described herein are a novel method and apparatus that permit measurement of the relative amount of saturated hydrocarbon oil and all unsaturated hydrocarbon oils that will not support a reaction in the presence of water or liquid immiscible with the oil. Numerous novel features of the inventive process and apparatus have been disclosed that are believed, for the first time, to enable accurate field-site measurement of small quantities of such oils in water and other liquids immiscible with oil. A preferred embodiment of the novel apparatus of the present invention has been disclosed as a means for carrying out the inventive process. Such apparatus provides a direct readout of relative oil content and permits such measurements to be made quickly and conveniently in the field by personnel having no special skill.

It will now be apparent to those familiar with the art to which the present invention pertains that in addition to the novel process and apparatus disclosed herein, certain novel features thereof have also been disclosed which although designed specifically for operation in the present invention, are readily adaptable to a variety of other uses not necessarily associated with the process of measuring oil content. By way of example, a novel electrode assembly has been disclosed and a novel magnetic stirring mechanism has been disclosed for use therewith. Both such features may be applied advantageously in other fields not necessarily related to the present invention. However, it will be understood that all such novel advantageous features, whether or not used in the process and apparatus of the present invention, are contemplated to be within the scope of the inventive contributions disclosed herein.

Having thus described a preferred embodiment of the invention what is claimed is:

1. A method of measuring relatively small amounts of hydrocarbon oil comprising:
   providing a sample which includes saturated hydrocarbon oil and a first liquid which is immiscible with the oil;
   providing an essentially nonconductive solvent which is essentially not soluble in the first liquid and which extracts the oil from the first liquid;
   providing a conductivity additive which renders hydrocarbon oil electrically conductive but does not render the solvent electrically conductive;
   mixing the sample, the solvent and the conductivity additive in a container to cause the solvent to extract oil from the first liquid to form a mixture including the oil, the solvent, and the conductivity additive with the conductivity additive rendering the oil of the mixture electrically conductive, said first liquid and said mixture having different specific gravities whereby said mixture and said first liquid are in essentially distinct layers in said container;
   passing said mixture between electrodes having a known voltage difference therebetween, after the oil is rendered conductive; and
   measuring the current induced between said electrodes to obtain an indication of the amount of oil in said mixture.

2. A method as defined in claim 1, wherein said conductivity additive includes colloidal metal-containing particles having a particle size of about 0.2 microns dispersed in the solvent.

3. An apparatus for measuring relatively small amounts of hydrocarbon oil contained in a liquid which is immiscible with the oil, the apparatus comprising:
   a mixing container for containing said oil and liquid,
   solvent means for separating said oil from said liquid to form a solvent-oil mixture in said container;
   means for adsorbing colloidal metal-containing particles on said hydrocarbon oil of said mixture in said container to render said hydrocarbon oil conductive without rendering said solvent conductive; and
   means for measuring the conductivity of said mixture including said metal-contaning particles to provide an indication of the relative amount of said hydrocarbon oil in said liquid.

4. The apparatus as defined in claim 3, wherein said conductivity measuring means comprises:
   a pair of electrodes having a gap therebetween in which said mixture, including said metal-containing particles may be caused to flow;
   means for applying a voltage difference between said electrodes across said gap; and
   means for providing a measurement indication dependent upon the current induced between said electrodes across said gap.

5. An apparatus for measuring relatively small amounts of hydrocarbon oil contained in a liquid which is immiscible with oil, the apparatus comprising:
   a mixing container for containing said oil and liquid,
   solvent means for separating said oil from said liquid to form a solvent-oil mixture in said container;
   means for adsorbing colloidal metal-containing particles on said hydrocarbon oil of said mixture in said container to render said hydrocarbon oil conductive without rendering said solvent conductive;
   electrode means for immersion in said mixture including said metal-containing particles;
   said electrode means comprising a pair of concentric cylinders radially spaced from one another to form a circumferential gap therebetween, and a pair of electrically isolated connecting rods for connecting said cylinders, respectively, to separate terminals of an electrical circuit; and
   an electrical circuit for connection to said rods and having means for applying a known voltage across said circumferential gap through said mixture including said metal-containing particles, and having means for amplifying the current induced in said gap and measuring said amplified current to provide an indication of the relative amount of said hydrocarbon oil in said liquid.

* * * * *